United States Patent [19]

Brown et al.

[11] Patent Number: 4,981,650
[45] Date of Patent: Jan. 1, 1991

[54] METHOD FOR TREATMENT OF DIOXIN-CONTAMINATED MEDIA

[76] Inventors: Terry L. Brown, 7831 Karakul La., Fayetteville, N.Y. 13066; Orest Hrycyk, 3593 Griffin Rd., Syracuse, N.Y. 13215; Cornelius B. Murphy, Jr., 4454 Kasson Rd., Syracuse, N.Y. 13215

[21] Appl. No.: 89,746

[22] Filed: Aug. 26, 1987

[51] Int. Cl.$^5$ ............................................. A61L 2/10
[52] U.S. Cl. .............................. 422/24; 260/DIG. 14
[58] Field of Search ................... 422/24; 260/DIG. 14

[56] References Cited

U.S. PATENT DOCUMENTS

| | | | |
|---|---|---|---|
| 4,280,012 | 7/1981 | Pastura et al. | 568/725 |
| 4,287,038 | 9/1981 | Geiser et al. | 204/158.21 |
| 4,327,027 | 4/1982 | Howard et al. | 549/349 |
| 4,446,236 | 5/1984 | Clyde | 435/813 |

OTHER PUBLICATIONS

Chem Abst. 103:21663d, Exner et al., "Hazard Waste", vol. 1(2), pp. 217–223, 1984.
Chem. Abst. 87:194950z, Gebefuegi et al., "Naturwissenschaft", vol. 64(9), pp. 486–487, 1977.
Chem. Abst., 106:107347c, Freeman et al., "Hazzard Mater", vol. 14(1), pp. 103–107, 1987.
Chem. Abst., 106:107348d, Des Rosiers, "J. Hazard Mater", vol. 14(1), pp. 119–133, 1987.
Abstract No. 379106—Chem Mark Rep, p. 4, 30 9/7/81.
Abstract No. 359345—Chem Eng., p. 17, 4/20/82—2,3,7,8.
Abstract No. 334058—Environ Sci Technol., p. 1163, Oct. 1980.
Liberti et al., "solar and UV Photodecomposition of 2,3,7,8-tetrachlorodibenzo-p-dioxin in the Environment", Science of the Total Environment, 10(2), 97–104 (Sept. 1978).
Bruner et al., "Gas Chromatographic Determination of 2,3,7,8-tetrachlorodibenzodioxin in the Experimental Decontamination of Seveso Soil by Ultraviolet Radiation", Analytical Chemistry, 50(6), 732–735 (May 1978).
"Destroying Dioxin: A Unique Approach", Waste Age 11(10), 60–63 (Oct. 1980).

Primary Examiner—Robert J. Warden
Assistant Examiner—Timothy M. McMahon
Attorney, Agent, or Firm—Woodcock, Washburn, Kurtz, Mackiewicz & Norris

[57] ABSTRACT

Methods for treating toxic chlorinated dibenzo-p-dioxin-contaminated media by photolytic degradation are disclosed. Soil contaminated wiht such toxins are contacted with a photolysis-activating agent such as 1-hexadecylpyridinium chloride and irradiated with UV radiation in the presence of one or more hydrogen donors.

4 Claims, 2 Drawing Sheets

METHOD FOR TREATMENT OF DIOXIN-CONTAMINATED MEDIA

BACKGROUND OF THE INVENTION

This invention relates to a method and apparatus for decontaminating media such as soil or chemical production wastes containing toxic chlorinated dibenzo-p-dioxins.

Chlorinated dibenzo-p-dioxins are a family of polycyclic aromatic compounds which consist of seventy-five unique congeners, which differ in their extent and sites of chlorination. The 2,3,7,8 tetrachlorodibenzo-p-dioxin congener, (2,3,7,8 TCDD), which is commonly and incorrectly referred to as dioxin, is of special environmental concern because it is one of the most toxic substances known to man. 2,3,7,8 TCDD can be acutely toxic to various mammals in single doses as low as a few micrograms per kilogram of body weight. There is a marked variation in species sensitivity towards 2,3,7,8-TCDD, for which the LD50 ranged from 0.6 ug/kg in the guinea pig to over 3,000 ug/kg in hamsters. In addition to being acutely toxic, lower doses of 2,3,7,8-TCDD can induce a variety of adverse responses including rapid weight loss, skin disorders, immune suppression, liver disease, porphyria and reproductive dysfunction. 2,3,7,8 TCDD has also been demonstrated to be highly teratogenic and is an extremely potent carcinogen.

Not all dioxins are capable of inducing toxic effects. Their toxic potential is related to the number and placement of chlorine atoms on the basic dioxin molecule. The structural requirement for toxicity appears to be substitution by chlorine in at least three of the four lateral positions (2,3,7,8) and the absence of chlorine at the non-lateral or "peri" (1,4,6,9) positions. A dramatic decrease in toxicity is observed as a result of any deviation from the 2,3,7,8 configuration. For the purposes of this invention, the dibenzo-p-dioxins substituted by chlorine in at least three of the four lateral positions shall be termed toxic chlorinated dibenzo-p-dioxins or toxic dioxins.

Dioxins are not produced for any commercial purpose, but are formed as unwanted contaminants during the synthesis and use of ortho-chlorinated phenols. They are also produced during the combustion of chlorinated organics and municipal refuse. There have been a number of industrial accidents where chlorophenol reactors have overheated and produced large amounts of dioxins. The most recent dioxin accident of this type occurred in 1976 in Seveso, Italy where an estimated 70 kg of 2,3,7,8-TCDD was released into an area populated by humans.

Although modern chlorophenol production processes limit the formation of dioxins, early techniques yielded significant amounts of dioxin by products. The herbicide 2,4,5-T and the germicide hexachlorophene, which utilized 2,4,5-trichlorophenol as an intermediate, often contained 2,3,7,8-TCDD. Technical grade pentachlorophenol has also been known to contain dioxins. Although it does not contain significant quantities of 2,3,7,8-TCDD, it has been shown to induce toxicity of the dioxin type, presumably due to other active dioxin congeners.

Dioxins and related compounds such as chlorinated dibenzofurans are also produced during the incineration of municipal wastes and possibly from the combustion of fossil fuels. Fly ash derived from municipal wastes typically contain 2,3,7,8-TCDD in the low part per billion range. Although dioxin yields are minor when compared to the levels produced during chlorophenol synthesis, combustion may represent a major source of dioxins due to the large volume of incineration and energy production currently taking place. Because of the potential toxicity of dioxins and dibenzofurans, refuse incinerators may soon be required to monitor the dioxin content of fly ash and airborne emissions and dispose of recovered particulates in an environmentally acceptable fashion.

Probably one of the most severe dioxin contamination problems emerging today is the discovery of sites in various portions of the country where chlorophenol production wastes have been disposed in an environmentally unsound manner. Chlorinated phenols have been and remain very important chemical intermediates. However, their process wastes such as sludges and reactor still bottoms can contain high levels of dioxins. Over the years, these wastes have been disposed of by various means including incineration, landfilling and even application to rural roads and fields as a means of dust control.

It is an object of this invention to provide a safe and effective means of treating toxic chlorinated dibenzo-p-dioxin-contaminated media, e.g., soil and chemical production wastes, to remove substantially all of such toxic dioxins from said media.

It is a further object of this invention to provide a device for on-site treatment of toxic chlorinated dibenzo-p-dioxin-contaminated media.

These and other objects of the invention will become apparent from the following description.

SUMMARY OF THE INVENTION

A method for treating toxic chlorinated dibenzo-p-dioxin-contaminated media to remove substantially all of said toxic dioxins has now been found. The method of this invention comprises exposing said media to a photolysis-activating agent and subsequently irradiating said activated media with ultraviolet radiation in the presence of one or more hydrogen donors, the intensity and duration of said irradiation and the amount of said hydrogen donor being effective to degrade substantially all of said toxic dioxin in said extract.

This invention also relates to a device for carrying out the above-described process. The device of this invention comprises means for receiving toxic dioxin-contaminated media and means for photolyzing the toxic dioxin-containing media to degrade substantially all of said toxic dioxin. Optionally, the device of this invention comprises means for contacting said toxic dioxin-contaminated media with a liquid medium capable of extracting therefrom substantially all of said dioxin and means for photolyzing the dioxin-containing extract to degrade substantially all of said toxic dioxin.

DETAILED DESCRIPTION OF THE INVENTION

The method and device of this invention utilize the photolytic degradation of toxic chlorinated dibenzo-p-dioxins as a means for decontaminating media containing such toxic compounds. When 2,3,7,8-TCDD is photolyzed, it degrades, for example, through mechanisms such as the nucleophilic displacement of chlorine in the presence of a suitable hydrogen donor. One of the major factors controlling the photolytic decontamination of toxic chlorinated dibenzo-p-dioxins is the activation efficiency of the dioxins in the media in which they are incorporated (e.g., soil, liquid or solid production wastes). These media can vary considerably at an uncontrolled disposal site. Due to the light absorbing and quenching effects of many media components, and the mass of the media compared to the amount of toxic chlorinated dibenzo-p-dioxin present, it is necessary to efficiently activate the toxic dioxin in the media. Activating agents for photolysis reactions are well known in the art and include such subclasses of agents as charge transfer agents and free radical initiators or stabilizing agents. An activating agent for use in this invention is the charge transfer agent 1-hexadecylpyridinium chloride although other useful agents may include substituted and unsubstituted benzophenone and other ketones, humic acid-containing substances, and cetylpyridinium chloride. The activating agents are, in effect, agents which catalyze the photolytic degradation of dioxin by facilitating the transfer of electronic charge from the dioxin to a proton donor.

In one embodiment of this invention, solid or liquid toxic dioxin-containing media are directly exposed to an effective amount of activating agent and are then photolyzed by exposure to intense ultraviolet irradiation in the presence of one or more hydrogen donors. High pressure mercury vapor lamps are used to provide the ultraviolet irradiation. The irradiation should generally be of a sufficient intensity and should be applied for a sufficient period of time to insure degradation of substantially all toxic dioxins. It is necessary to introduce a hydrogen donor such as an alcohol (e.g., methanol or isopropyl alcohol), a fatty acid (e.g., vegetable oil) or a fat (e.g., olive oil) to the activated media during photolysis. The amount of hydrogen donor introduced should be at least stoichiometrically equivalent to the amount of toxic dioxin in the extract, but is preferably substantially more.

In another embodiment of this invention, the solid or liquid toxic dioxin-containing media is subjected to an extraction step prior to the photolysis step. The media is contacted with a liquid capable of extracting therefrom the toxic dioxins, and the resulting extract is then treated as described above to effect photolytic degradation of the dioxin. Non-polar liquids such as, but not limited to, hexane, methylene chloride and toluene, are the preferred extractants for use in this invention.

Figure 1:
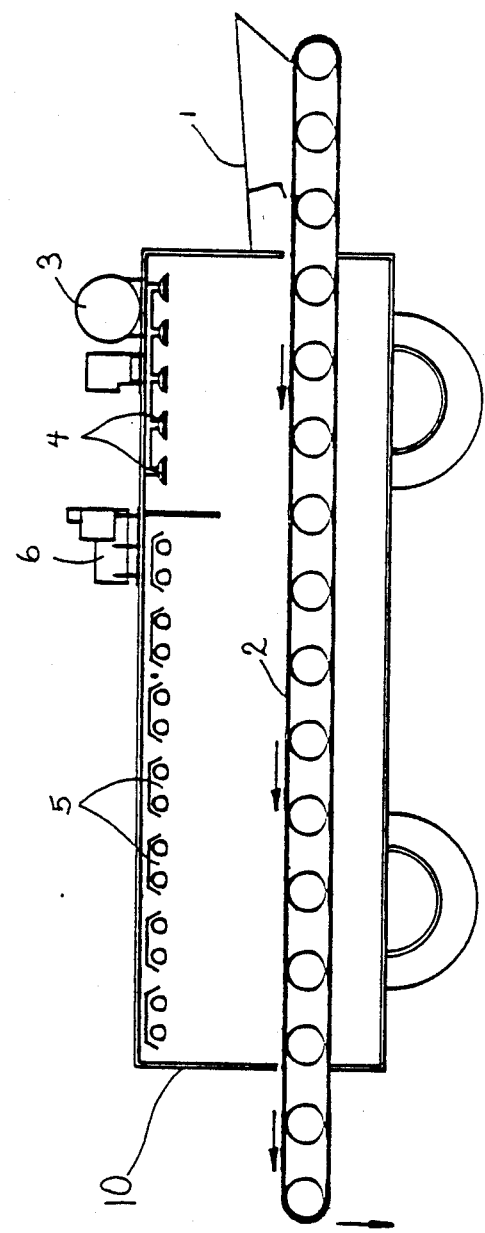
FIG. 1 is a cross-sectional view of an embodiment of a device for carrying out the method of this invention which does not utilize a solvent extraction step.
Figure 2:
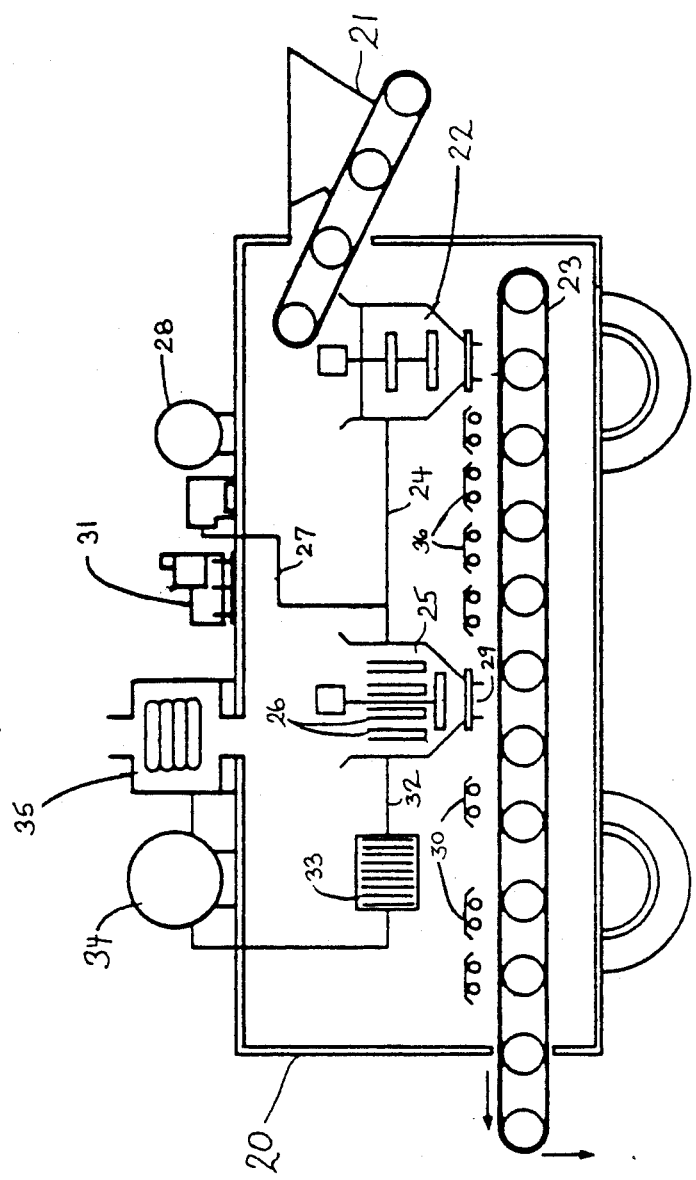
FIG. 2 is a cross-sectional view of an embodiment of a device for carrying out the method of this invention which utilizes a solvent extraction step.

Specific embodiments of treatment devices useful for carrying out the process of this invention are illustrated in cross-section in FIGS. 1 and 2. The treatment device 10 shown in cross-section in FIG. 1 is useful for carrying out the method of this invention which does not utilize an extraction step. Treatment device 10 contains delivery system 1, such as a hopper and screen, which deliver the toxic dioxin-contaminated media to device 10. The contaminated media are deposited onto a surface, such as conveyor system 2, on which they may be exposed to activating agent and ultraviolet radiation. To insure exposure of all of the contaminated media to ultraviolet radiation, the media are preferably agitated and mixed by mechanical means. Activating agent and hydrogen donor may be applied to the contaminated media on conveyor system 2 through nozzles 4 which spray activating agent and hydrogen donor received from feed system 3 onto the media. By virtue of conveyor system 2 moving in the direction indicated by the arrows, the activating agent-exposed contaminated media is moved under ultraviolet lamps 5 which are powered by power supply 6. The intensity of lamps 5 and the speed at which conveyor system 2 moves are controlled so that photolytic degradation of toxic dioxin in the contaminated media is substantially complete by the time said media completes its pass through treatment device 10 and is deposited outside the device.

Treatment device 20 illustrated in cross-section in FIG. 2 is useful for carrying out the method of this invention which utilizes an extraction step. Treatment device 20 comprises a delivery system 21 for delivering toxic dioxin-contaminated media to the device 20. Said media is transported to extraction reactor 22 which contains a liquid capable of extracting from said media the toxic dioxins. This extracting solvent may also comprise the hydrogen donor required in the overall process. Alternatively, a suitable hydrogen donor may be added to the extracting solvent or later on during addition of the activating agent. Following extraction of the dioxins, solids in the contaminated media are separated from the dioxin-containing media, e.g., by settling, and are deposited onto conveyor system 23 which moves in the direction indicated by the arrows. The solids on conveyor system 23 are subjected to irradiation with infrared lamps 36 to enhance evaporation of extraction liquids from said solids. The dioxin-containing liquid extract in reactor 22 is transported through line 24 to photolysis reactor 25 which contains immersion UV lamps 26. Activating agent from feed system 28 is added through line 27 to the extract as it enters photolysis reactor 25. The liquid extract is held in reactor 25 until substantially all of the toxic dioxin therein is photolytically degraded. Any soil remaining in the extract in reactor 25 is then deposited onto conveyor system 23 where it may optionally be subjected to additional UV irradiation by passing under UV lamps 30. This additional irradiation insures substantially complete degradation of the toxic dioxins. The extraction solvent (containing degraded toxic dioxins) remaining in reactor 25 is passed through line 32 to a filter 33 on its way to solvent recovery system 34 and extraction solvent storage system 35 from which it may be recycled.

What is claimed is:

1. A method of decontaminating a toxic chlorinated dipenzo-p-contaminated soil media comprising contacting said media with 1-hexadecylpyridinium chloride and irradiating said resulting media with ultraviolet radiation in the presence of one or more hydrogen donors, the intensity and duration of said irradiation and the amount of said hydrogen donors being effective to degrade substantially all of said toxic dioxin in said media.

2. The method of claim 1 where said dioxin is 2,3,7,8 tetrachlorodibenzo-p-dioxin.

3. A method of decontaminating a toxic chlorinated dibenzo-p-dioxin-contaminated soil media comprising contacting said media with a liquid medium in which said toxic dioxin is soluble to form a toxic dioxin-containing extract, contacting said extract with 1-hexadecylpyridinium chloride and irradiating the resulting extract with ultraviolet radiation in the presence of one or more hydrogen donors, the intensity and duration of said irradiation and the amount of said hydrogen donors being effective to degrade substantially all of said toxic dioxin in said extract.

4. The method of claim 3 where said dioxin is 2,3,7,8-tetrachlorodibenzo-p-dioxin.

* * * * *